United States Patent [19]

Green et al.

[11] Patent Number: 5,288,888
[45] Date of Patent: Feb. 22, 1994

[54] PROCESS FOR THE SYNTHESIS OF ACETIC ACID, (DIMETHOXYPHOSPHINYL) [[1,1-DIMETHYLETHYL)DIMETHYLSILYL]-OXY]-, (4-NITROPHENYL) METHYL ESTER

[75] Inventors: Kenneth E. Green, Pearl River; Edward R. Ruso, Nanuet; Mellard N. Jennings, Highland Falls, all of N.Y.; Alex R. Jurgens, Westfield; David M. Blum, Upper Saddle River, both of N.J.; Gregg B. Feigelson, Spring Valley, N.Y.

[73] Assignee: American Cyanamid Company, Wayne, N.J.

[21] Appl. No.: 53,283

[22] Filed: Apr. 28, 1993

[51] Int. Cl.$^5$ ............................ C07F 7/08; C07F 7/18
[52] U.S. Cl. .................................................. 556/405
[58] Field of Search ......................................... 556/405

[56] References Cited

U.S. PATENT DOCUMENTS

| | | | |
|---|---|---|---|
| 4,804,770 | 2/1989 | Karanewsky | 556/405 |
| 4,992,429 | 2/1991 | Ulrich et al. | 556/405 X |
| 5,017,716 | 5/1991 | Karanewsky et al. | 556/405 |
| 5,210,110 | 5/1993 | Rutsch et al. | 556/405 X |

OTHER PUBLICATIONS

D. Horne, J. Gaudino, and W. J. Thompson, Tetrahedron Letters, vol. 25, No. 33, 3529–3532, Apr. 1984; "A Method for the Synthesis of α-Ketoesters from Aldehydes".

E. Nakamura, Tetrahedron Letters, vol. 22, 663–666, Jun. 1981; "New Acyl Anion Equivalent".

F. Texier-Boullet and A. Foucaud, Synthesis, 916, Sep. 1982; "Synthesis of 1-Hydroxyalkanephosphonic Esters on Alumina".

*Primary Examiner*—Paul F. Shaver

[57] ABSTRACT

The invention is an improved process for the large scale production of acetic acid, (dimethoxyphosphinyl) [[1,1-dimethylethyl)dimethylsilyl]oxy]-, (4-nitrophenyl)-methyl ester.

8 Claims, No Drawings

PROCESS FOR THE SYNTHESIS OF ACETIC ACID, (DIMETHOXYPHOSPHINYL) [[1,1-DIMETHYLETHYL)DIMETHYLSILYL]-OXY]-, (4-NITROPHENYL) METHYL ESTER

SUMMARY OF THE INVENTION

The invention provides an improved process for the large scale production of acetic acid, (dimethoxyphosphinyl)[[1,1-dimethylethyl)dimethylsilyl]oxy]-, (4-nitrophenyl)methyl ester having the structural formula:

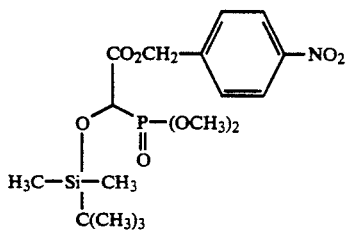

BACKGROUND OF THE INVENTION

The acetic acid, (dimethoxyphosphinyl)[[1,1dimethylethyl)dimethylsilyl]oxy]-, (4-nitrophenyl)methyl ester is an important intermediate for reaction with the aldehyde 2-azetidineacetaldehyde, 3-[1-[[(1,1-dimethylethyl)dimethylsilyl]oxy]ethyl]-4-oxo-1-(triethylsilyl)-,[2R-[2a,3b(R*)]] to prepare novel 2-substituted-3-carboxy carbapenem antibiotics as described in copending application Ser. No. 672,496, filed Mar. 20, 1991.

Methods for the synthesis of a-ketoesters from aldehydes are described by D. Horne, J. Gaudino and W. J. Thompson, Tetrahedron Letters, 25, 3529–3532 (1984). The synthesis of various a-alkoxyphosphonoacetates are described by E. Nakamura, Tetrahedron Letters, 22, 663–666 (1981). The synthesis of 1-hydroxyalkanephosphonic esters is described by F. Texier-Boullet and A. Foucaud, Synthesis, 916 (1982).

While these methods are sufficient for laboratory scale synthesis, our requirements are for a procedure amenable to large-scale work and ideally that the products of each step be crystalline.

It has now been found that acetic acid, (dimethoxyphosphinyl)[[1,1-dimethylethyl)dimethylsilyloxy]-, (4-nitrophenyl)methyl ester can be advantageously synthesized in four steps from L-tartaric acid in high overall yield with acceptable purity. This compound is used to prepare novel substituted-3-carboxy protected carbapenem antibiotics which can be easily deprotected to the carboxylic acid by catalytic reduction.

By using acetic acid, (dimethoxyphosphinyl)[[1,1-dimethylethyl)dimethylsilyl]oxy]-, (4-nitrophenyl)-methyl ester in the reaction with the aldehyde 2-azetidine-acetaldehyde, 3-[1-[[(1,1-dimethylethyl)dimethylsilyl]oxy]ethyl]-4-oxo-1-(triethylsilyl)-, [2R[2a,3b(R*)]], the resulting 4-nitrophenyl ester of the compound can be advantageously deprotected catalytically without poisoning of the catalyst.

The process comprises reaction of L-tartaric acid with p-nitrobenzylbromide in the presence of triethylamine in N,N-dimethylformamide at 0°–5° C. and recovering the 2,3-dihydroxy-butanedioic acid bis-(4-nitrophenyl)ester produced as a solid. The 2,3-dihydroxy-butanedioic acid bis-(4-nitrophenyl)ester is oxidized with periodic acid in tetrahydrofuran at room temperature and the product dihydroxyacetic acid 4-nitrophenyl ester recovered as a solid. The dihydroxy acetic acid 4-nitrophenyl ester is reacted with dimethyl phosphite in ethyl acetate at reflux temperature and the product acetic acid, (dimethoxyphosphinyl)hydroxy-, (4-nitrophenyl)methyl ester isolated as a solid. The acetic acid, (dimethoxyphosphinyl)hydroxy,(4-nitrophenyl)methyl ester is reacted with t-butyldimethylsilyl chloride in the presence of imidazole in N,N-dimethylformamide at room temperature and the desired acetic acid, (dimethoxyphosphinyl)[[1,1-dimethylethyl)dimethylsilyl]oxy]-, (4-nitrophenyl)methyl ester recovered as a solid.

DETAILED DESCRIPTION

The process and compounds of the present invention are described in the following reactions of Scheme I:

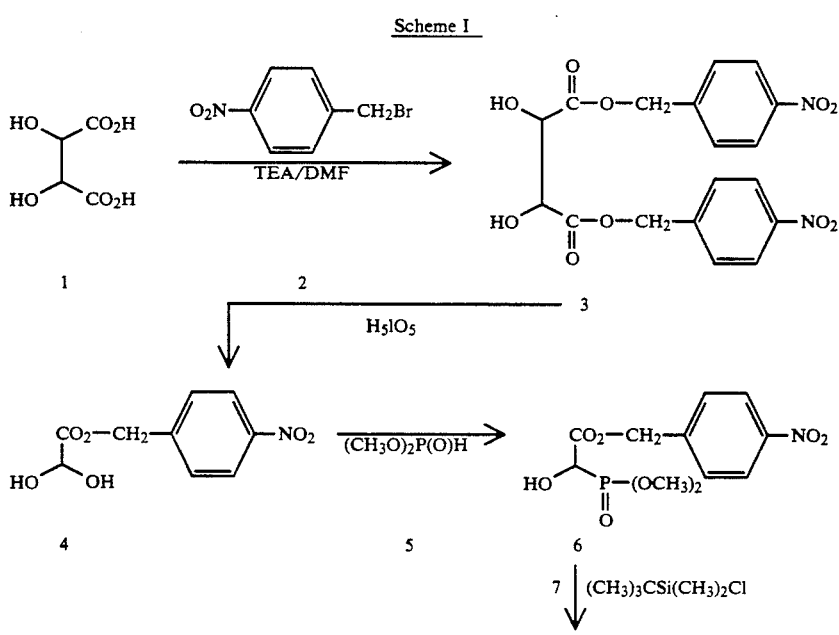

Scheme I

-continued

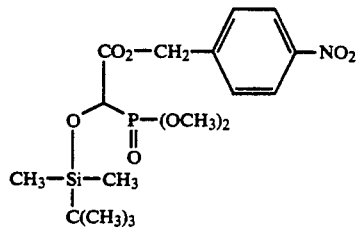

8

In accordance with the above reaction scheme, L-tartaric acid 1 is diesterified by reaction with p-nitrobenzylbromide 2 in the presence of triethylamine (TEA) in N,N-dimethylformamide (DMF) for 5 hours at 0°–5° C. The slow sequential addition of the triethylamine and a solution of p-nitrobenzylbromide in N,N-dimethylformamide as well as careful control of the temperature is important for producing a high yield. Quenching the reaction mixture in ice and water and recovery of the solid by filtration gives the 2,3-di-hydroxy-butanedioic acid bis-(4-nitrophenyl)ester 3 in at least an 85% yield.

The 2,3-dihydroxy-butanedioic acid bis-(4-nitrophenyl)ester 3 is oxidized by reaction with periodic acid, $H_5IO_6$ in tetrahydrofuran (THP) at room temperature over 30 minutes. Other oxidants such as lead tetraacetate as described by G. J. P. Chittenden, Carbohydrate Res. 84, 350 (1980) and ozone as described by M. E. Jung, K. Shishido and L. H. Davis, J. Org. Chem. 47, 891 (1982) are unacceptable for large-scale reactions for practical reasons and difficulty in handling. The use of periodic acid is described by R. S. Schmid, J. D. Bryant, M. Dowlatzedah, J. I. Phillips, D. E. Prather, R. E. Schantz, N. L. Sear, and C. S. Vianco, J. Org. Chem. 56, 4056 (1991). Because periodic acid is not very soluble in tatrahydrofuran it is difficult to predict how concentrated this reaction can be performed. However, we have surprisingly found that by operating at concentrations consistent with desirable throughput levels (18% w/w tartrate to tetrahydrofuran), the reaction proceeds smoothly. The reaction mixture is filtered to remove inorganics, diluted with water, seeded and the solid glyoxalate collected. The cake is washed with heptane and dried to afford the desired dihydroxyacetic acid 4-nitrophenyl ester 4.

The most common protocols for driving reversible additions to aldehyde moieties to completion involves some form of water removal and/or acid catalysis. Indeed, the references of D. Horne, J. Gaudino, and W. J. Thompson Tetrahedron Letters, 25, 3529 (1984) and E. Nakamura, Tetrahedron Letters 22, 663 (1981) use both of these approaches. However, attempts to use these methods to condense 4 with 5 using p-toluenesulfonic acid catalysis and water removal via benzene azeotrope produces side reactions. Compound 6 can never be obtained in acceptable yield and is never possible to obtain in a pure, crystalline form. We have surprisingly found that acid catalysis and water removal is unnecessary and refluxing 4 with 5 in ethyl acetate reproducibly affords 6.

The dihydroxyacetic acid 4-nitrophenyl ester 4 is best reacted with dimethylphosphite 5 in ethyl acetate at reflux for 5 hours. The reaction solution is evaporated and the residue dissolved in ethyl acetate, then diluted with hexanes and seeded. Cooling affords the desired acetic acid, (dimethoxyphosphinyl)-hydroxy-, (4-nitrophenyl)methyl ester 6 after collection of the solid by filtration, washing the cake with 2:1 ethyl acetate-hexanes and drying.

The acetic acid, (dimethoxyphosphinyl)-hydroxy-, (4-nitrophenyl)methyl ester 6 is reacted, using the method of E. J. Corey and A. Venkateswarlu, J. Amer. Chem. Soc. 94, 6190 (1972), with t-butyldimethylsilyl chloride 7 in N,N-dimethylformamide (DMF) in the presence of imidazole at room temperature over 5 hours. A mixture of 2:1 ethyl acetate-water is added to the reaction mixture. The organic layer is separated, washed with saturated sodium bicarbonate, dried and the solvent removed in vacuo.

The resulting material is slurried in 1:3 ethyl acetate-heptane to give a faint yellow, cyrstalline solid after filtration. Final purification is achieved by dissolving the product in 50° C. ethyl acetate/heptane (1:1) and filtering through hydrous magnesium silicate. Upon evaporation of the solvent, the desired acetic acid (dimethoxyphosphinyl) [[1,1-dimethylethyl)dimethylsilyl]oxy]-, (4-nitro- phenyl)methyl ester 8 is obtained as a crystalline solid.

The following non-limiting examples illustrate the process of the present invention as well as the preparation of novel compounds.

EXAMPLE 1

2,3-Dihydroxy-butanedioic acid bis-(4-nitrophenyl)ester

A stirred solution of 750.5 g of L-tartaric acid in 2.8 L of N,N-dimethylformamide is cooled to 0°–5° C. and 1062 g of triethylamine added dropwise over 2 hours while maintaining the temperature at 0°–5° C. A solution of 2160 g of p-nitrobenzylbromide in 4.68 L of N,N-dimethylformamide is added dropwise over a 5 hour period while maintaining the temperature at 0°–15° C. The reaction mixture is quenched with 9 L of water and 4.0 kg of ice then stirred for 2 hours. The product is collected by filtration, air dried then stirred with 5 L of ethanol. The solid is collected by filtration and collected to give 1.79 kg (85%) of the desired product, m.p. 163°–164° C.

$^1H$ NMR (300 MHz, DMSO-$d_6$) d 8.23 (d,4H,J=8.76 Hz), 7.68(d,4H,J=8.6 Hz), 5.86(d,2H,J=8.1 Hz), 5.34(s,4H), 4.68(d,2H,J=9.0 Hz); $^{13}C$ NMR (75.5 MHz, DMSO-$d_6$) d 171.10, 147.05, 143.84, 128.30, 123.49, 72.64, 64.78; MS(CI, NH$_3$): m/z 438 (M+NH$_4$)+.

EXAMPLE 2

Dihydroxyacetic acid 4-nitrophenyl ester

A solution of 630.5 g of 2,3-dihydroxybutanedioic acid bis-(4-nitrophenyl)ester in 3.8 L of tetrahydrofuran is stirred for 20 minutes. While stirring, 410.3 g of periodic acid is added portionwise over 30 minutes. The reaction mixture is filtered and 13.3 L of water added to the filtrate. The reaction mixture is cooled to 50° C. and a seed crystal of dihydroxy-acetic acid 4-nitrophenyl aster added. The resulting mixture is allowed to stand at 50° C. for 24 hours. The product is collected by filtration and the cake washed with 3 L of water followed by 3 L of heptane to yield 554 g (81%) of the desired product, m.p. 100°-102° C.;

$^1$H NMR (300 MHz, DMSO-d$_6$) d 8.25(d,2H,J=8.9 Hz), 7.66(d,2H,J=8.9 Hz), 6.82(d,2H,J=7.5 Hz), 5.30(s,2H), 5.13(t,1H,J=7.6 Hz); $^{13}$C NMR (75.5 MHz, DMSO-d$_6$) d 170.16, 147.08, 143.75, 128.39, 123.53, 86.84, 64.27; MS(CI, NH$_3$): m/z 210(M - H$_2$O+H)+.

EXAMPLE 3

Acetic acid, (dimethoxyphosphinyl)hydroxy-, (4-nitrophenyl)methyl ester

A solution of 454.3 g of dihydroxyacetic acid 4-nitrophenyl ester and 330.2 g of dimethyl phosphite in 2.3 L of ethyl acetate is brought to reflux and stirred for 5 hours. The volatiles are removed in vacuo and the residue is dissolved in 800 ml of ethyl acetate. The solution is diluted with 400 ml of hexanes and a seed crystal of acetic acid, (dimethoxyphosphinyl)hydroxy, (4-nitrophenyl)methyl ester added. Cooling to 50° C. for 24 hours affords a solid which is filtered and washed with 2:1 ethyl acetate-hexanes to yield 492 g (77%) of the desired product, m.p. 83.5°-84.5° C.;

$^1$H NMR (300 MHz, CDCl$_3$) d 8.25(d,2H,J=8.8 Hz), 7.59(d,2H,J=S.S Hz), 5.41(dd,2H,J=13.3 Hz), 4.70(d,1H, J$_{P-C-H}$=16.52 Hz), 3.86(d,3H,J$_{P-O-CH}$=10.6 Hz), 3.83(d,3H,J$_{P-O-CH}$=10.8 Hz), 3.61(br s,1H); $^{13}$C NMR (75.5 MHz, CDCl$_3$) d 168.59, 147.74, 141.88, 128.33, 123.59, 68.52(d,J$_{P-C}$=155.4 Hz), 66.31, 54.50(d,J$_{P-O-C}$=7.1 Hz), 54.17(d,J$_{P-O-C}$=6.8 Hz); MS(CI, NH$_3$): m/z 320(M+H)+.

EXAMPLE 4

Acetic acid, (dimethoxphoshinyl)[[1,1-dimethylethyl)-dimethylsilyl-loxyl-, (4-nitrophenyl)methyl ester To 5.83 L of N,N-dimethylformamide is added 1436.4 g of acetic acid, (dimethoxyphosphinyl)hydroxy-, (4-nitrophenyl)methyl ester followed by 847.85 g of t-butyldimethylsilyl chloride and 842.5 g of imidazole. The reaction mixture is stirred for 2 hours and 10 L of ethyl acetate and 5 L of water added. The organic layer is separated and washed with 5 L of water, 5 L of saturated aqueous sodium bicarbonate and 5 L of brine. After drying the organic layer with anhydrous Na$_2$SO$_4$, the solvent is removed in vacuo to afford 2275 g of crude material which is slurried with 2 L of ethyl acetate and 6 L of heptane and filtered to yield 1407 g of the desired product as a faint yellow crystalline solid. Final purification is achieved by dissolving the solid in 10 L of 1:1 ethyl acetate-heptane, heating to 50° C. and filtering through 1440 g of hydrous magnesium silicate. The cake is washed with 3×2 L of 1:1 ethyl acetate-heptane. The solvent is removed in vacuo to provide 1321 g (68%) of the desired product as a crystalline solid. m.p. 93.5°-94.5° C.

$^1$H NMR (300 MHz, CDCl$_3$) d 8.24(d,2H,J=6.9 Hz), 7.60(d,2H,J=8.8 Hz), 5.35(dd,2H,J=13.3 Hz), 4.72(d,1H, J$_{P-C-H}$=18.7 Hz), 3.84(d,3H,J =10.9 Hz), 3.81(d,3H,J$_{P-O-CH}$=10.8 Hz), 0.92(s,9H), 0.11(s,3H), 0.10(s,3H); $^{13}$C NMR (75.5 MHz, CDCl$_3$) d 167.71, 147.36, 142.17, 128.14, 123.31, 70.11(d,J$_{P-C}$=161.8 Hz), 53.82 (d,J$_{P-O-C}$=7.1 Hz), 53.67(d,J$_{P-O-C}$=6.7 Hz), 25.12, 17.92; MS(CI,NH$_3$): m/z 451 (M+NH$_4$)+.

We claim:

1. A process for the preparation of a compound of the formula:

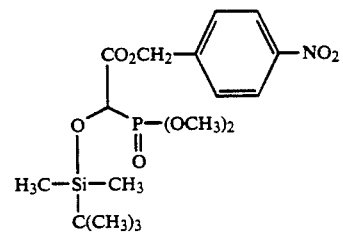

which comprises the steps of (a) reaction of L-tartaric acid of the formula:

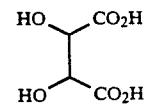

with p-nitrobenzylbromide in the presence of an amine in a solvent to the corresponding bis-(4-nitrophenyl)-ester of the formula:

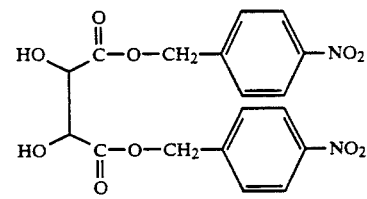

(b) oxidizing the bis-(4-nitrophenyl)ester with an oxidant in a solvent to product the dihydroxyacetic acid 4-nitrophenyl ester of the formula:

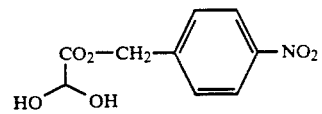

(c) reacting the dihydroxyacetic acid 4-nitrophenyl ester with dimethylphosphite in a solvent to produce the dimethoxyphosphinyl compound of the formula:

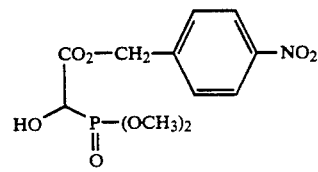

(d) reacting the dimethoxyphosphinyl compound with t-butyldimethylsilyl chloride in a solvent in the presence of a base to afford the desired compound of the formula:

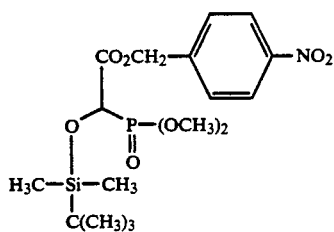

2. A process according to claim 1, wherein the solvent of step (a) is N,N-dimethylformamide.

3. A process according to claim 2, wherein the amine of step (a) is triethylamine.

4. A process according to claim 3, wherein the oxidant of step (b) is periodic acid.

5. A process according to claim 4, wherein the solvent of step (b) is tetrahydrofuran.

6. A process according to claim 5, wherein the solvent of step (c) is ethyl acetate.

7. A process according to claim 6, wherein the solvent of step (d) is N,N-dimethylformamide.

8. A process according to claim 7, wherein the base of step (d) is imidazole.

* * * * *